United States Patent
Toya et al.

(10) Patent No.: US 10,267,712 B2
(45) Date of Patent: Apr. 23, 2019

(54) CENTRIFUGAL SMEARING DEVICE AND SEALED ROTATING CONTAINER

(71) Applicants: Sakura Seiki Co., Ltd., Nagano (JP); Sakura Finetek Japan Co., Ltd., Tokyo (JP)

(72) Inventors: Matsumi Toya, Nagano (JP); Tadashi Toufukuji, Nagano (JP)

(73) Assignees: SAKURA SEIKI CO., LTD., Chikuma-shi (JP); SAKURA FINETEK JAPAN CO., LTD., Tokyo (JP)

( * ) Notice: Subject to any disclaimer, the term of this patent is extended or adjusted under 35 U.S.C. 154(b) by 0 days.

(21) Appl. No.: 14/778,016

(22) PCT Filed: Mar. 7, 2014

(86) PCT No.: PCT/JP2014/056075
§ 371 (c)(1),
(2) Date: Sep. 17, 2015

(87) PCT Pub. No.: WO2014/167926
PCT Pub. Date: Oct. 16, 2014

(65) Prior Publication Data
US 2016/0274005 A1    Sep. 22, 2016

(30) Foreign Application Priority Data
Apr. 9, 2013   (JP) .................................. 2013-081441

(51) Int. Cl.
*G01N 1/28*   (2006.01)
*B01L 1/00*   (2006.01)
(Continued)

(52) U.S. Cl.
CPC ............ *G01N 1/2813* (2013.01); *B01L 3/508* (2013.01); *B01L 9/52* (2013.01); *B04B 5/0407* (2013.01);
(Continued)

(58) Field of Classification Search
CPC ....................................................... G01N 1/10
See application file for complete search history.

(56) References Cited

U.S. PATENT DOCUMENTS 4,391,710 A  *  7/1983  Gordon ................. B04B 5/0421
                                                                210/361
5,252,228 A     10/1993  Stokes et al.

FOREIGN PATENT DOCUMENTS

JP            57110352          7/1982

OTHER PUBLICATIONS

Watanuki Patent Service Bureau, "European Search Report", EP Application No. 14783426.1, (dated Oct. 19, 2016).

* cited by examiner

*Primary Examiner* — Kathryn Wright
(74) *Attorney, Agent, or Firm* — William Thomas Babbitt; Leech Tishman Fuscaldo & Lampl, Inc.

(57) ABSTRACT

A centrifugal smearing device including a sealed rotating container that houses a chamber with a slide glass removably attached for holding a liquid sample to smear cells with a centrifugal force onto the slide glass, and a base housing the sealed rotating container and including rotational driving means for rotating the sealed rotating container, the sealed rotating container includes a main body capable of housing the chamber and a lid for closing an upper surface opening portion of the main body, a seal portion for sealing a space between the main body and the end face of the upper face opening portion is provided on an outer circumferential edge of the lid, and a scattering protection wall is formed at an (Continued)

inside of the seal portion so as to protrude downward to hide the seal portion from inside so that a liquid does not scatter onto the seal portion.

2 Claims, 11 Drawing Sheets

(51) Int. Cl.
  *B04B 5/10* (2006.01)
  *B04B 7/02* (2006.01)
  *B04B 5/04* (2006.01)
  *B04B 7/06* (2006.01)
  *B01L 3/00* (2006.01)
  *B01L 9/00* (2006.01)
  *B04B 7/08* (2006.01)

(52) U.S. Cl.
  CPC ............... *B04B 5/10* (2013.01); *B04B 7/02* (2013.01); *B04B 7/06* (2013.01); *B04B 7/08* (2013.01); *B01L 2200/0689* (2013.01); *B01L 2300/041* (2013.01); *B01L 2300/0848* (2013.01); *B04B 2007/025* (2013.01); *G01N 2001/2846* (2013.01)

FIG.2

CENTRIFUGAL SMEARING DEVICE AND SEALED ROTATING CONTAINER

CROSS-REFERENCE TO RELATED APPLICATIONS

The present patent application is a national phase application of International Application No. PCT/JP2014/056075, filed Mar. 7, 2014, which claims priority to Japanese Application No. 2013-081441, filed Apr. 9, 2013, the disclosures of which are incorporated herein by reference.

TECHNICAL FIELD

The present invention relates to a centrifugal smearing device for smearing floating cells of a liquid sample onto a slide glass and a sealed rotating container used for the centrifugal smearing device.

BACKGROUND ART

For example, a centrifugal smearing device has been known for performing centrifugation on liquid collected from body fluid, blood, and urine to obtain cells, and smearing the separated cells onto a slide glass.

Patent Literature 1 discloses a conventional centrifugal smearing device. FIG. 12 illustrates the conventional centrifugal smearing device. The conventional centrifugal smearing device includes a base 2 including a motor 1, and a sealed rotating container 3 that is mounted in the base 2 and rotated by drive of the motor 1.

In the sealed rotating container 3, a plurality of chambers 4 for holding a liquid sample can be housed. The slide glass can be mounted to the chamber 4 with a holder.

The sealed rotating container 3 has a main body 7 and a lid 8 for covering an upper face opening portion of the main body 7. Inside the main body 7, a rotor 6 for disposing the chamber 4 is provided.

At an upper end edge portion of the main body 7 is formed with a planar portion 9 projecting outward and a protruding portion 5 projecting upward at a leading end portion of the planar portion 9.

The lid 8 has a planar portion 17 whose outer edge portion projects outward, and a seal member 18 such as rubber provided at a leading end portion of the planar portion 17.

When the main body 7 is covered with the lid 8, a planar portion 6 of the lid 8 is placed on the planar portion 9 of the upper end edge portion of the main body 7. Further, a seal member 18 of the lid 8 comes into contact with the protruding portion 5 of the main body 7. With this arrangement, a seal portion is constituted between the main body 7 and the lid 8 to prevent liquid from leaking from an inside of the main body 7 to an outside thereof.

A funnel-shaped holding section for holding the liquid is formed in a chamber, and a passage directed outward is formed on a side face of a bottom portion of the holding section. When the chamber is rotated to apply a centrifugal force to the liquid sample, the liquid sample passes through this passage to move outward. An opening portion is formed at an outside of the passage, and the slide glass is arranged at an outward of the opening portion.

Between the opening portion and the slide glass, a rubber packing or filter paper is arranged to seal space between the opening portion and the slide glass. When the filter paper is arranged, since the cells are smeared onto the slide glass and liquid components seep out through the filter paper, limited floating cells in the liquid sample can be efficiently collected.

CITATION LIST

Patent Literature

PTL 1: Japanese Patent Laid-Open No. 62-39014

SUMMARY OF INVENTION

Technical Problem

As described above, when the filter paper is used for the chamber, it is advantageous for collecting the floating cells, but the liquid components separated during being centrifuged scatter from the chamber.

The liquid sample generally is the body fluid, urine, or blood of a patient. Thus, since the liquid sample may cause infection, caution is required for dealing with the liquid sample.

Therefore, when the separated liquid components scatter from the chamber, caution is required so that the liquid components do not leak outside the sealed rotating container.

However, the conventional sealed rotating container described in Patent Literature 1 has a wall face in a slightly tapered shape so that a diameter of the sealed rotating container becomes slightly larger toward the upper portion of a main body. Therefore, it can be considered that the liquid components scattered from the chamber seep out from an inside of the main body to a planar portion of an upper end edge portion of the main body. In this case, it can be also considered that the liquid components seep into a seal portion between the planar portion of the main body and a planar portion of a lid.

As described above, if the liquid components seep into the seal portion, the liquid components increased with the centrifugal force may exceed a sealing force in the seal portion to leak outside the sealed rotating container.

Further, if the liquid components seep into the seal portion, for example, when an operator opens the lid, the liquid components may come into contact with the operator.

To solve the problem described above, the purpose of the present invention is to provide the centrifugal smearing device in which the liquid components do not leak outside the sealed rotating container, and the sealed rotating container.

Solution to Problem

A centrifugal smearing device of the present invention includes: a sealed rotating container that houses a chamber with a slide glass removably attached for holding a liquid sample and smearing cells in the liquid sample onto the slide glass with a centrifugal force; and a base housing the sealed rotating container and having rotational driving means for rotating the sealed rotating container, wherein said sealed rotating container includes a main body being capable of housing said chamber and a lid configured to close an upper face opening portion of the main body, wherein a seal portion for sealing a space between the main body and an end face of the upper face opening portion of the main body is provided at an outer circumferential edge of said lid, and wherein a scattering protection wall is formed at an inside of the seal portion so as to protrude downward to hide the seal portion from inside so that a liquid does not scatter onto the seal portion.

By adopting the construction described above, it is possible to prevent the liquid scattered from the chamber from coming into contact with the scattering protection wall and scattering onto the seal portion. Therefore, the liquid can be prevented from leaking outside the main body of the sealed rotating container.

A sealed rotating container of the present invention, which is used for a centrifugal smearing device and houses a chamber with a slide glass removably attached for holding a liquid sample and smearing cells in the liquid sample onto the slide glass with a centrifugal force, includes: a main body being capable of housing said chamber: and a lid configured to close an upper face opening portion of the main body, wherein a seal portion for sealing a space between the main body and an end face of the upper face opening portion of the main body is provided at an outer circumferential edge of said lid, and wherein a scattering protection wall is formed at an inside of the seal portion so as to protrude downward to hide the seal portion from inside so that a liquid does not scatter onto the seal portion.

By adopting the construction described above, it is possible to prevent the liquid scattered from the chamber from coming into contact with the scattering protection wall and scattering onto the seal portion. Therefore, the liquid can be prevented from leaking outside the main body of the sealed rotating container.

Further, the scattering protection wall may be formed tilting outward.

By adopting the construction described above, the liquid scattering onto the scattering protection wall drops obliquely downward outside along the scattering protection wall due to a centrifugal force and the construction tilting outward so that the liquid can be prevented from intruding into the seal portion.

Further, the seal portion of the lid may include a packing placed on a planar face formed on the end face of the upper opening portion of the main body.

As described above, it is possible to ensure sealing property and easy attachment and removal of the lid by mounting the packing at a side of the lid.

Advantageous Effects of Invention

According to the centrifugal smearing device and the sealed rotating container of the present invention, the liquid components can be prevented from leaking outside the sealed rotating container.

BRIEF DESCRIPTION OF DRAWINGS

FIG. 2 is a cross-sectional view illustrating a constitution of a sealed rotating container of the present invention

DESCRIPTION OF EMBODIMENTS

Figure 1:
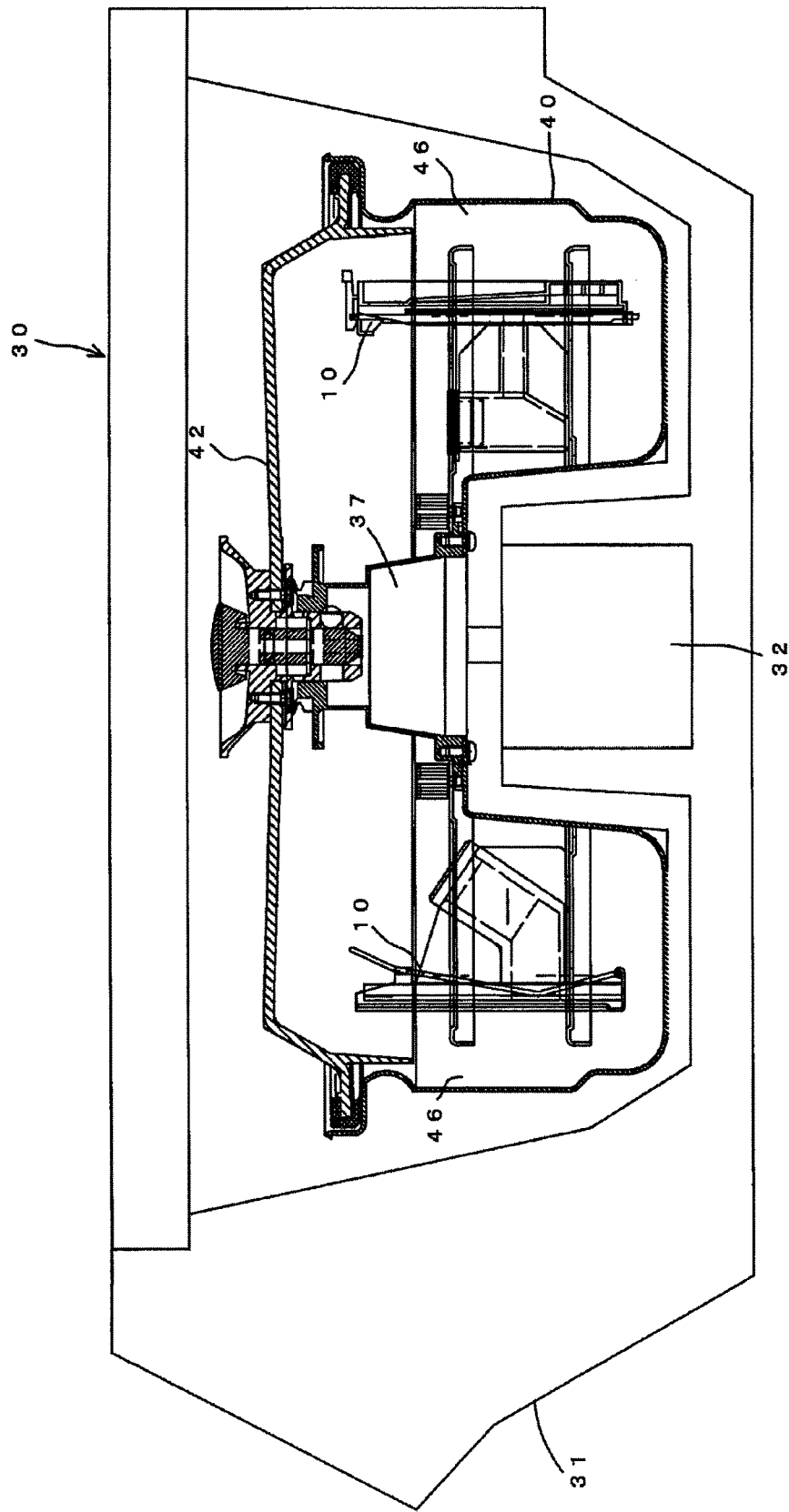
FIG. 1 is a cross-sectional view illustrating a constitution of a centrifugal smearing device of the present invention.

FIG. 1 illustrates a side face of a centrifugal smearing device according to the present embodiment.

A centrifugal smearing device 30 includes a base 31 including a motor 32 functioning as rotation driving means and a sealed rotating container 34 to be stored in the base 31. FIG. 1 illustrates a schematic constitution of the base 31.

A piece 37 is mounted to a rotational axis of the motor 32 of the base 31. The sealed rotating container 34 is arranged such that the piece 37 enters a housing 35 formed in a center of the sealed rotating container 34. By rotational driving of the motor 32, the sealed rotating container 34 is rotated via the piece 37.

Figure 2:
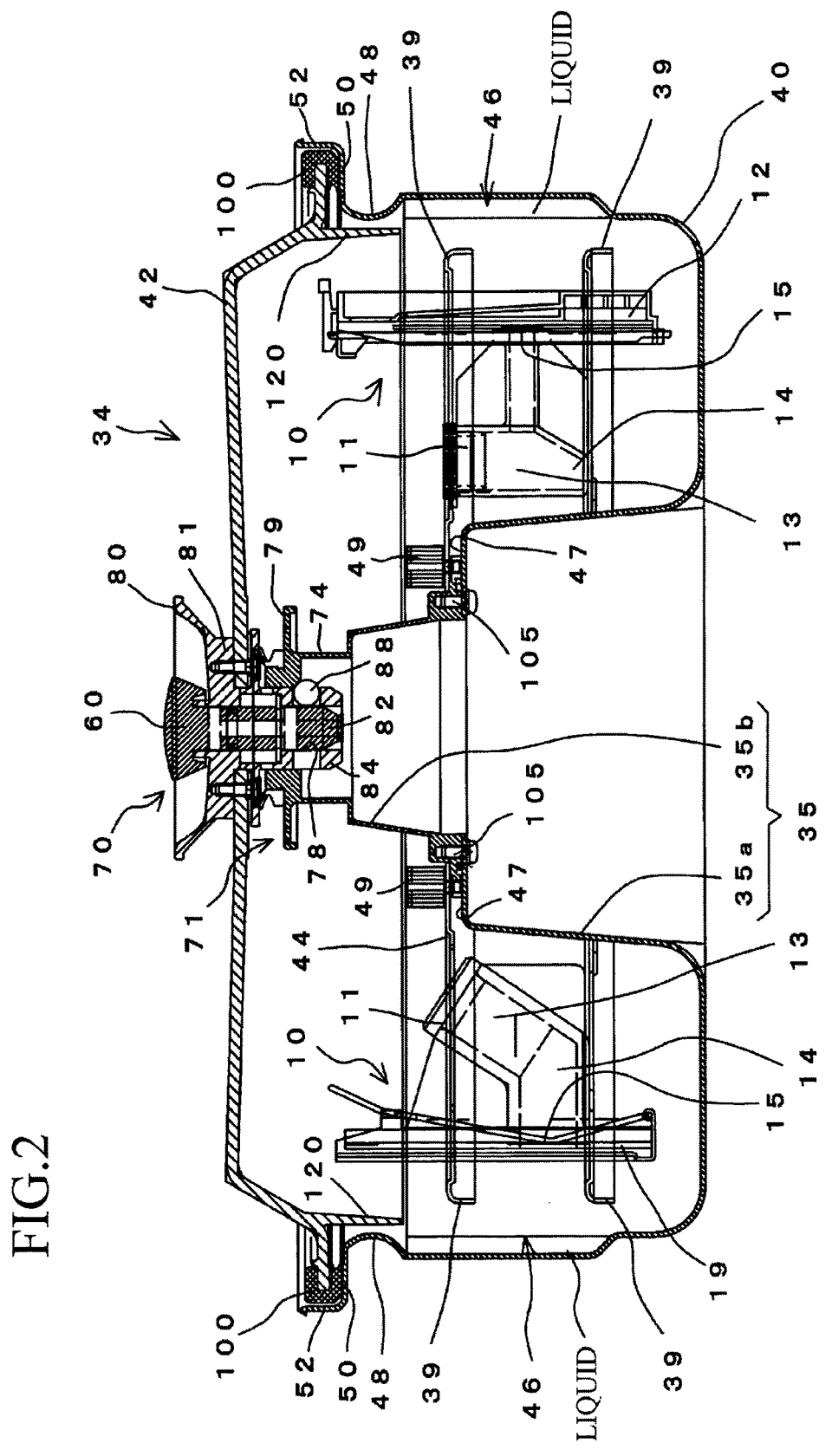
Figure 3:
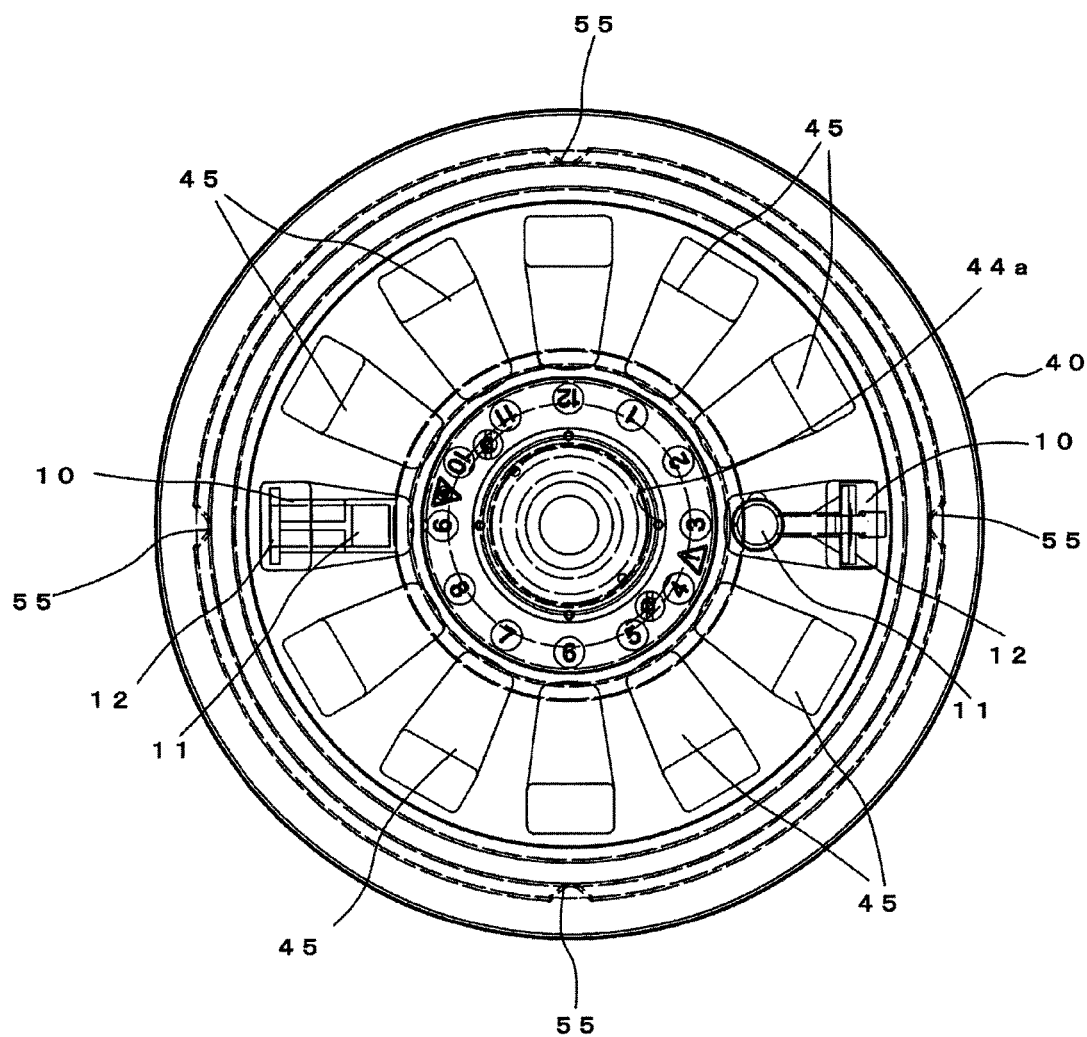
FIG. 3 is a plan view of a main body of the sealed rotating container.
Figure 4:
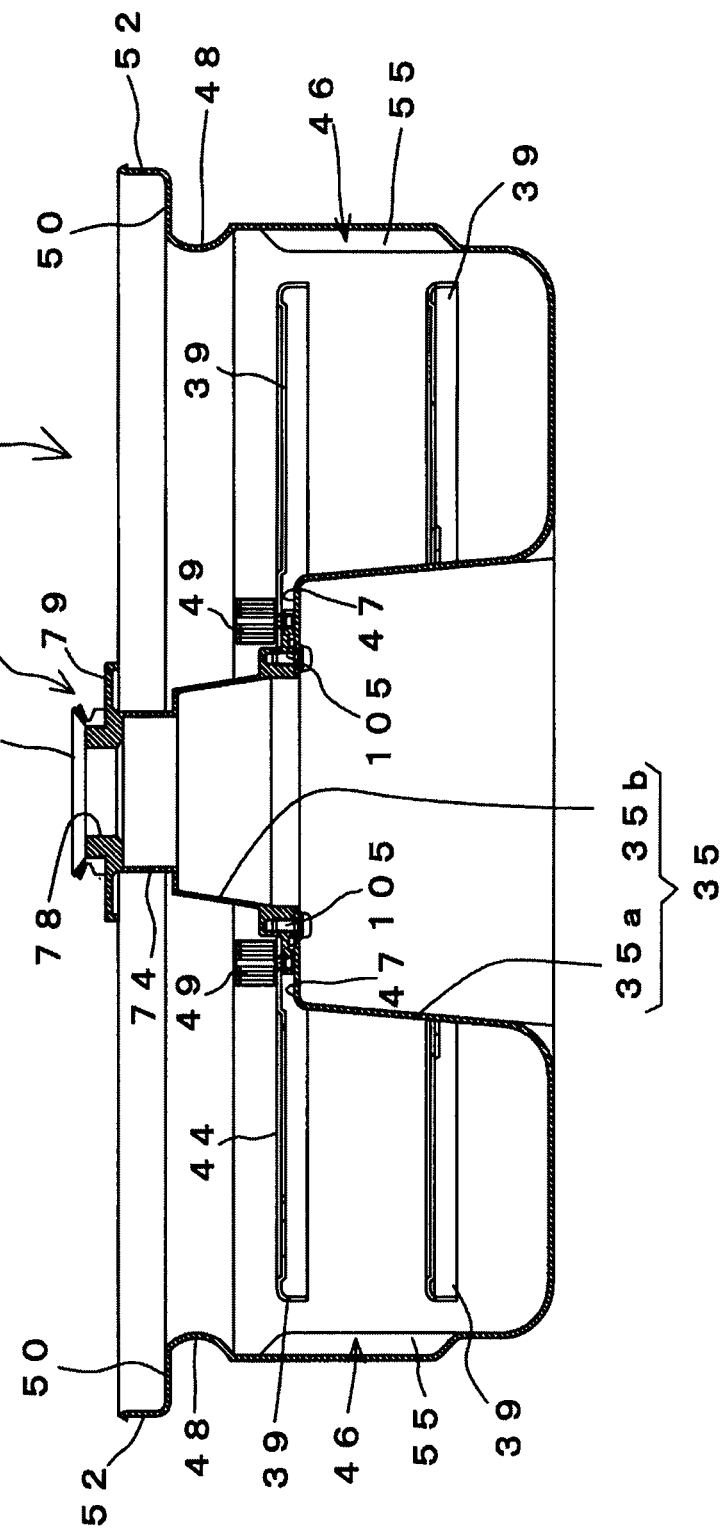
FIG. 4 is a cross-sectional view of the main body of the sealed rotating container.

FIG. 2 illustrates a side face view of the sealed rotating container, and FIG. 3 illustrates a plan view thereof. FIG. 4 illustrates a side face view of only the main body of the sealed rotating container.

The sealed rotating container 34 includes a main body 40 into which the chamber 10 can be housed, and a lid 42 for closing and sealing an upper face opening portion of the main body 40.

The main body 40 is a member in a container-like shape, and is formed as a housing 35 whose center portion is raised upward to be mounted to the base 31. Therefore, an outer circumferential portion other than the center portion of the main body 40 functions as a housing section in a ring-like shape.

The housing 35 has a lower stage portion 35a for housing a portion in which the motor 32 and so on of the base 31 are arranged and an upper stage portion 35b for housing the piece 37 described above. The upper stage portion 35b has a diameter smaller than that of the lower stage portion 35a. Therefore, a stepped portion 47 is formed between a lower end of the lower stage portion 35a and an upper end of the upper stage portion 35b.

The lower stage portion 35a and the upper stage portion 35b are constituted by different members from each other, and the lower stage portion 35a and the upper stage portion 35b are mounted with each other via a mounting screw 105.

On a further upper portion of the upper stage portion 35b for housing the piece 37 of the housing 35, a mounting portion 71 to which the lid 42 is mounted is formed. At the upper end portion of the mounting portion 71, a "V" ring 110 that comes into close contact with the lid 42 to ensure sealing property is provided.

The mounting portion 71 has a cylindrical raised portion 74 projecting upward from the upper stage portion 35b of the housing 35 and an insertion portion 78 through which a fixing hub 84 (described below) provided in a knob portion 70 (described below) of the lid 42 is inserted. An outer wall of the insertion portion 78 is formed with a gripping portion 79 projecting outward.

Reasons why the gripping portion 79 is formed in a center of the main body 40 is as follows.

Namely, when a sample having a low infection level is adopted or the chamber 10 sealed with rubber is adopted, or when a small amount of sample is used, the sealed rotating container 34 can be used to perform the centrifugal smearing processing without mounting the lid 42.

In such a case, when the operator operates as holding the main body 40, the operator can operate as gripping a gripping portion 79 provided at a center portion of the main body 40.

Further, in the main body 40, a rotor 44 to which the plurality of chambers 10 can be mounted is removably arranged.

An opening portion 44a is formed at a center of the rotor 44. By inserting the upper stage portion 35b of the housing 35 into the opening portion 44a in the center of the rotor 44 and disposing a circumferential edge of the opening portion 44a on the stepped portion 47, the rotor 44 is mounted to the main body 40.

Further, at the circumferential edge of the opening portion 44a of the rotor 44, a thumb screw 49 is provided at a plurality of points. With the thumb screw 49, the circumferential edge of the opening portion 44a of the rotor 44 and the stepped portion 47 of the main body 40 are fixed with each other.

The rotor 44 includes two substantially disk-shaped members 39, 39 in a planar view at a predetermined interval in the vertical direction. The two disk-shaped members 39, 39 are formed with a plurality of rectangular holes 45 for mounting the chamber.

The rectangular holes 45 are formed to communicate the two disk-shaped members 39, 39 with each other, and an upper portion and a lower portion of the chamber 10 inserted into the rectangular hole 45 are supported by the two disk-shaped members 39, 39 to be fixed to the rotor 44.

Further, the plurality of rectangular holes 45 has a substantially trapezoidal shape in a planar view. A long side of the rectangular hole 45 is located in a diameter direction of the disk and a short side thereof is located in the circumferential direction of the disk. The plurality of rectangular holes 45 is formed at uniform positions with respect to a center of the disk, and kept in balance during being rotated.

Next, the chamber 10 will be described. The constitution of the chamber 10 used for the centrifugal smearing device of the present invention is not limited to any specific constitution, but a known constitution can be adopted. The chambers illustrated in FIGS. 1 to 3 are formed in different types depending on the right or the left, but they have a basically same function.

A general chamber that can be used for the present invention includes the holding section 11 for holding a liquid sample and a holder 12 for gripping a slide glass 19.

The holding section 11 has an upward-downward circulation portion 13 opening upward and a storage section 14 opening to a side of the holder 12.

In a vicinity of the opening portion 15 opening from the storage section 14 to the side of the holder 12, a packing made of rubber, for example, or filter paper can be arranged (not illustrated). The packing is used to ensure the sealing property of the opening portion 15. Further, by arranging the filter paper, while the liquid components of the liquid sample are absorbed, the flowing cells separated from the liquid components can be smeared onto the slide glass 19.

Even if the filter paper is arranged in the chamber 10, when a large amount of the liquid sample is held in the holding section 11, the liquid sample may scatter into the sealed rotating container 34 through the filter paper during being centrifuged. According to the constitution of the sealed rotating container 34 described below, the scattered liquid components can be stored.

The main body 40 of the sealed rotating container 34 has a storage section 46 for storing the liquid components (hereinafter, may be simply referred to as "liquid") scattered from the chamber 10.

The storage section 46 is constituted such that the inside face of the main body 40 projects outward (outward recessed). A wall face of the storage section 46 is constituted as a vertical wall face in the vertical direction. Therefore, even if the centrifugal force is applied to the liquid stored in the storage section 46, the liquid does not receive the force in a direction where the liquid goes up.

The upper end portion of the storage section 46 is formed with a protruding portion 48 projecting inward. By forming the protruding portion 48, the liquid stored in the storage section 46 can be restricted from moving upward.

The protruding portion 48 of the present embodiment is a constriction viewed from an outside of the main body 40. By recessing a metal member constituting the main body 40 from the outside, the protruding portion 48 projecting inward is formed. However, as the protruding portion of the present invention, another member different from the member constructing the main body 40 may be mounted on the upper end portion of the storage section 46 to form the protruding portion 48.

An upper portion of the protruding portion 48 of the main body 40 is formed with the planar portion 50 for placing the lid 42. The planar portion 50 is a horizontal face directed outward. The outer edge portion of the planar portion 50 is a folded portion 52 folded upward.

The outer edge of the lid 42 and the packing (described below) are disposed on the planar portion 50 and the folded portion 52 to constitute the seal portion of the sealed rotating container 34.

Next, the unbalanced-load prevention mechanism provided in the storage section will be described.

In the set number of rotations of the sealed rotating container 34, there is a plurality of vibrational resonance points. In other words, a plurality of vibrational resonance points is passed from starting rotation to a maximum number of rotations, and further a plurality of vibrational resonance points is passed also from the maximum number of rotations to stop the rotation. At the vibrational resonance points, the sealed rotating container 34 easily loses balance, and the liquid stored in the storage section 46 may get over the protruding portion 48 to enter the seal portion. Further, a problem of danger may occur in which the sealed rotating container 34 loses the balance to cause the sealed rotating container 34 to rotate as rattling in the base 31.

The present embodiment adopts a constitution in which load of the liquid stored in the storage section 46 does not become unbalanced so that not only specifically the vibrational resonance points but the sealed rotating container 34 are rotated in balance.

Figure 5:
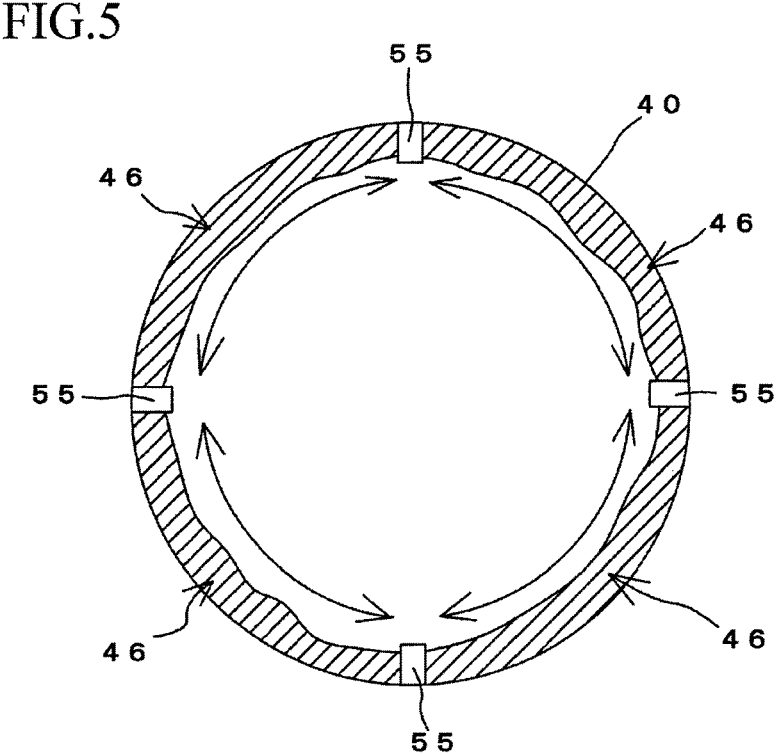
FIG. 5 illustrates a function of an unbalanced-load prevention mechanism.

FIG. 4 illustrates a side face of the sealed rotating container when the unbalanced-load prevention mechanism is provided. FIG. 5 illustrates a schematic view of a state of the liquid stored in the storage section when the unbalanced-load prevention mechanism is provided.

According to the present embodiment, the unbalanced-load prevention mechanism includes a plurality of ribs 55 projecting inward from the wall face of the storage section 46 and extending in the vertical direction. The rib 55 illustrated herein has a rectangular shape in its cross-section, but, as illustrated in FIG. 3, may be formed in a mountain-like shape formed of a curve in its cross-section.

Since the plurality of ribs 55 extends in the vertical direction, they have a function for dividing the liquid stored in the storage section 46 in the circumferential direction. Therefore, the liquid in the storage section 46 can be prevented from becoming unbalanced in the circumferential direction.

An upper end portion of each rib 55 in the vertical direction is preferably formed up to a position of the protruding portion 48 at least. By arranging as described above, the liquid in the storage section 46 can be prevented from getting over the protruding portion 48.

FIG. 5 illustrates a state where the ribs 55 are provided at four points, and arranged at the uniform positions. However, the number of the ribs 55 is not limited to four, but any number can be adopted. The intervals between the ribs 55, 55 need to be equal.

Figure 6:
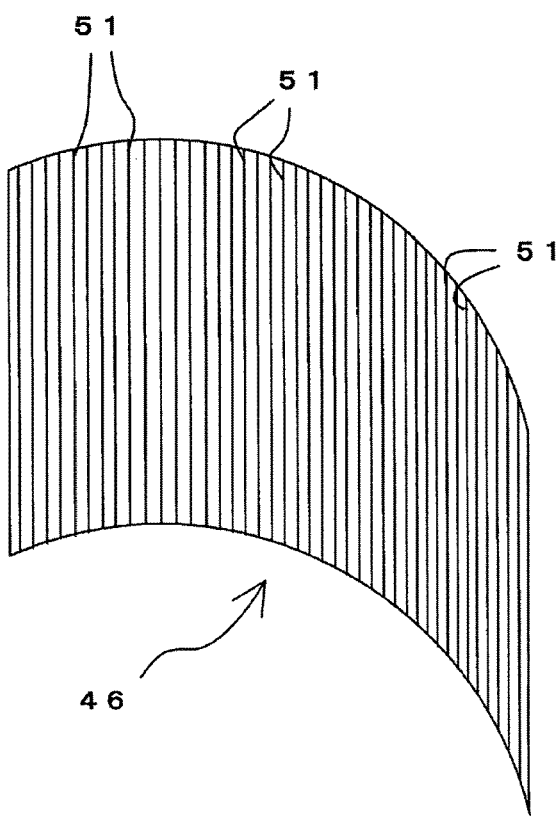
FIG. 6 illustrates another embodiment of the unbalanced-load prevention mechanism.

Subsequently, another embodiment of the unbalanced-load prevention mechanism will be described. FIG. 6 illustrates a part of the inner wall face of the storage section 46.

According to the embodiment, the inner wall face of the storage section 46 is formed with fine irregularities. With the irregularities, the frictional resistance between the liquid in the storage section 46 and the inner wall face of the storage section 46 is increased to disturb movement of the liquid in the storage section 46, thereby preventing the unbalanced load. As the example described herein, grooves 51 having a depth of about 1 mm and a width of about 1 mm are formed at a predetermined interval on the inner wall face of the storage section 46 along the vertical direction. As described above, by forming the irregularities in stripes extending in the vertical direction, the unbalanced-load prevention function for the liquid stored in the storage section 46 can be attained.

Further, another embodiment of the unbalanced-load prevention mechanism will be described.

Figure 7:
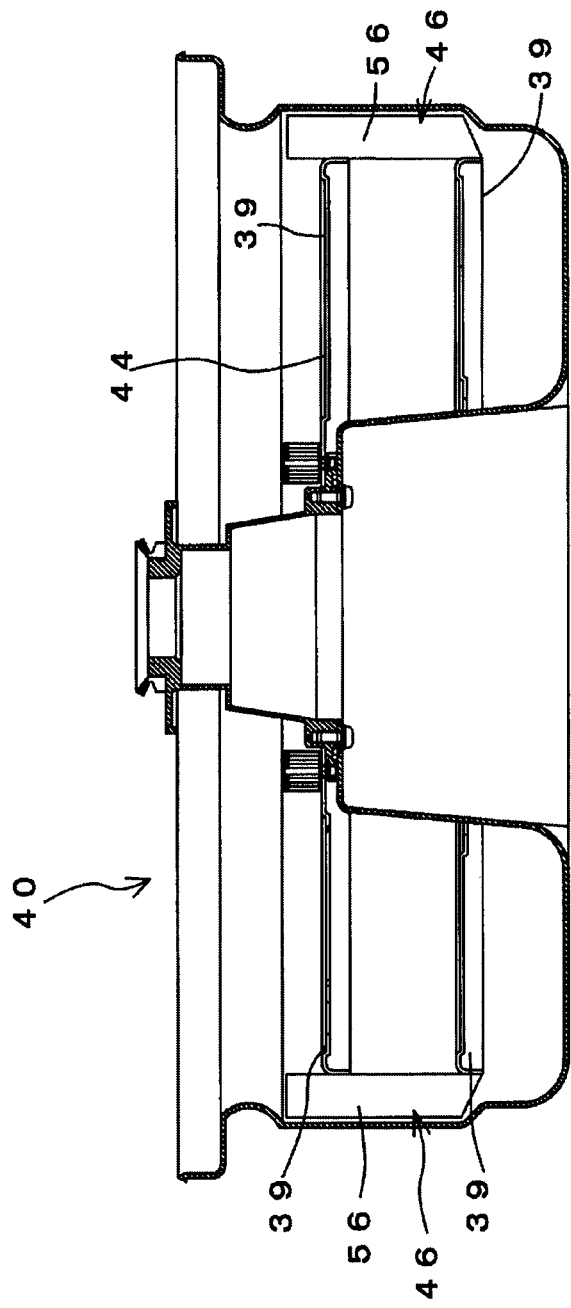
FIG. 7 is a cross-sectional view illustrating another embodiment of the unbalanced-load prevention mechanism.

FIG. 7 illustrates a state where the outer circumferential edge of the rotor 44 is provided with a plurality of dividers 56 projecting outward.

A length of the divider 56 in the diameter direction is the length thereof that enters the storage section 46, and the divider 56 is formed not to come into contact with the wall face of the storage section 46.

A length of the divider 56 in the vertical direction is the length thereof that can enter the storage section 46, and formed as long as possible. The divider 56 divides the liquid in the storage section 46 to perform a function in a similar manner to that of the rib 55 described above. In other words, the divider 56 has a function for dividing the liquid stored in the storage section 46 in the circumferential direction. Therefore, the liquid in the storage section 46 can be prevented from generating unbalance in the circumferential direction.

FIG. 7 illustrates a state where the dividers 56 are provided at four points, and arranged at the uniform positions. However, the number of the dividers 56 is not limited to four, but any number can be adopted. The intervals between the dividers 56, 56 need to be equal.

The above-described ribs 55 and fine irregularities (grooves 51) are directly formed on the main body 40 of the sealed rotating container 34.

However, the ribs 55 and the grooves 51 may be constituted as another member different from that of the main body 40. For example, as illustrated in FIG. 8, a cylindrical member 58 divided into a plurality of portions in the circumferential direction is provided to be mounted in the storage section 46, and the plurality of ribs 55 may be formed on the inner wall face of the member.

Similarly, to be mounted in the storage section 46, on the inner wall face of the cylindrical member 58 divided into the plurality of pieces in the circumferential direction, the fine irregularities (grooves 51) may be formed for increasing the frictional resistance between the liquid in the storage section 46 and the inner wall face of the storage section 46 (not illustrated).

Figure 8:
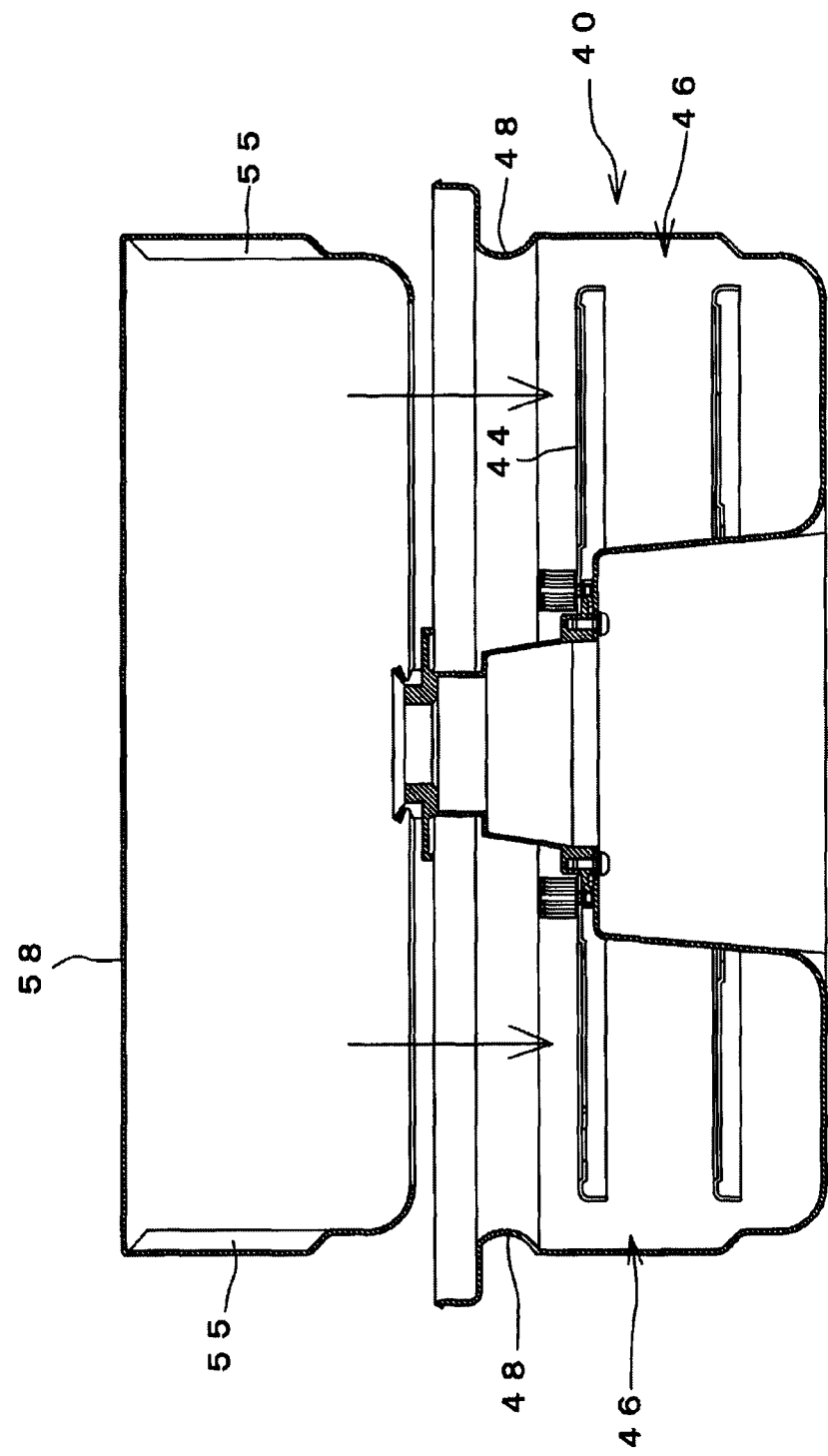
FIG. 8 is a cross-sectional view illustrating another embodiment of the unbalanced-load prevention mechanism.

The member 58 illustrated in FIG. 8 may be mounted in the storage section 46, and it may not be specifically divided in the circumferential direction.

Further, when the unbalanced-load prevention mechanism is provided as another body different from the storage section 46, it is not limited to a constitution to mount the member as illustrated in FIG. 8 in the main body 40, but only the rib 55 may be constituted as anther body different from the storage section 46 and mounted in the storage section 46.

Figure 9:
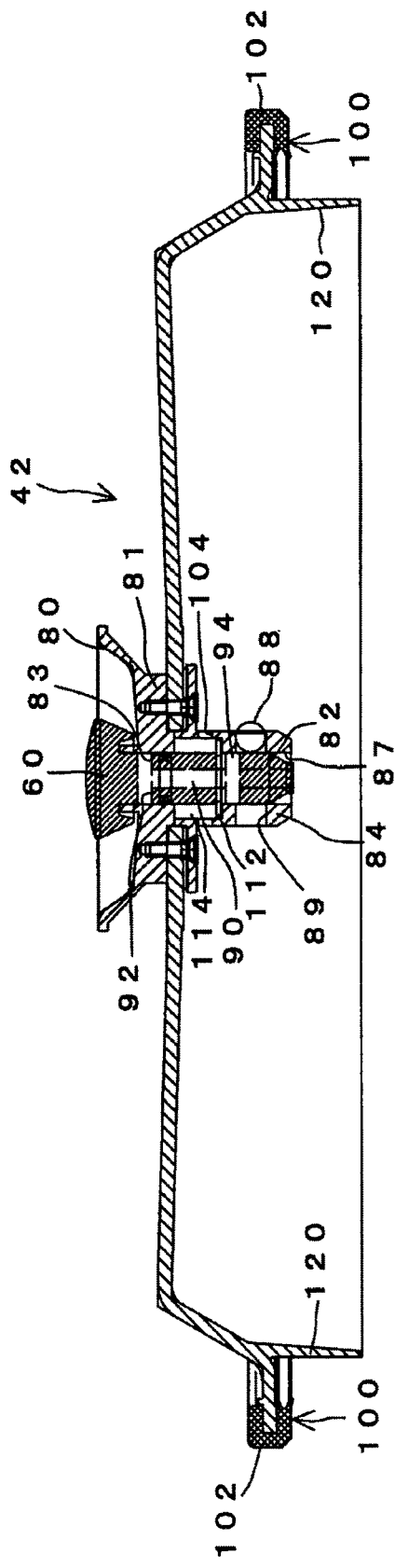
FIG. 9 is a cross-sectional view of a lid of the sealed rotating container.

Next, with reference to FIG. 9, a constitution of the lid will be described.

The lid 42 is constituted to completely cover and seal the upper face opening portion of the main body 40. The lid 42 is formed of transparent material such as strengthened glass or strengthened plastic so that an inside state can be observed.

First, the seal portion of the lid will be described.

The lid 42 is formed with a seal portion 100 for being placed on the planar portion 50 of the main body 40. The seal portion 100 is a site where the outside edge of the lid 42 is a horizontal plane and projects outward. At a leading end portion of the seal portion 100 (leading end of the outer edge portion of the lid 42), a packing 102 having a U-like shape in its cross section is mounted in such a manner to sandwich the seal portion 100 of the lid 42. The packing 102 is made of rubber. As described above, the packing 102 is mounted at a side of the lid 42 to ensure sealing property of the seal portion 100 and also easy attachment and removal of the lid 42.

A thickness of the packing 102 is formed as a thickness enough to house the packing 102 in the folded portion 52 of the planar portion 50 of the main body 40.

Further, an inside of the seal portion 100 of the lid 42 is formed with a scattering protection wall 120 for hiding and protecting the seal portion 100 from the inside, so that the liquid does not scatter onto the seal portion 100.

The scattering protection wall 120 projects downward from the inner wall face of the lid 42 and is formed in a ring-like shape making a circle at a lower portion of the lid 42. The scattering protection wall 120 has a function of protection not to allow the scattered liquid to enter a side of the seal portion 100 and also a function to flow the received liquid downward.

The scattering protection wall 120 may slope toward an outside. In other words, when the liquid scattered during the centrifugal smearing processing comes into contact with the scattering protection wall 120, a force for moving outward is applied by the centrifugal force. At this point, since the scattering protection wall 120 slopes toward the outside, the liquid drops outside, obliquely downward along the scatter protection wall. Since, outside, obliquely downward from the scattering protection wall 120, the storage section 46 is formed, the dropped liquid is stored in the storage section 46.

Figure 10:
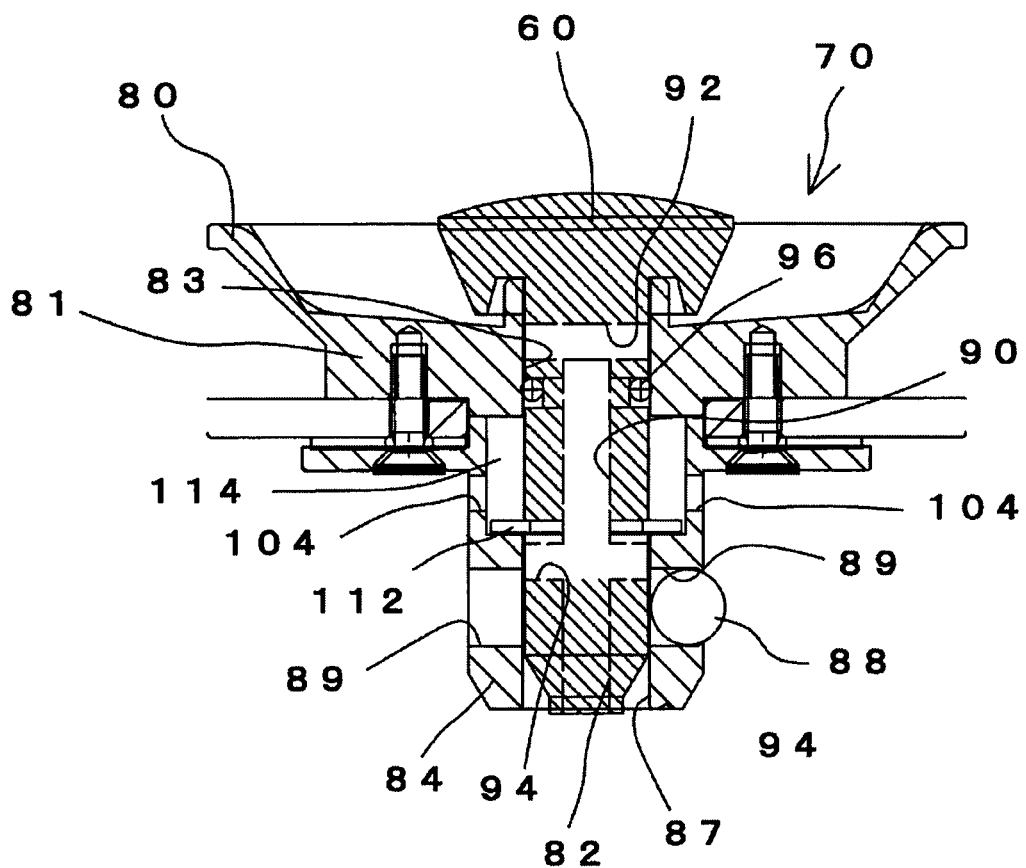
FIG. 10 is an enlarged view of a knob portion of the lid.

Next, a knob portion of the lid will be described. FIG. 10 illustrates an enlarged knob portion.

Figure 11:
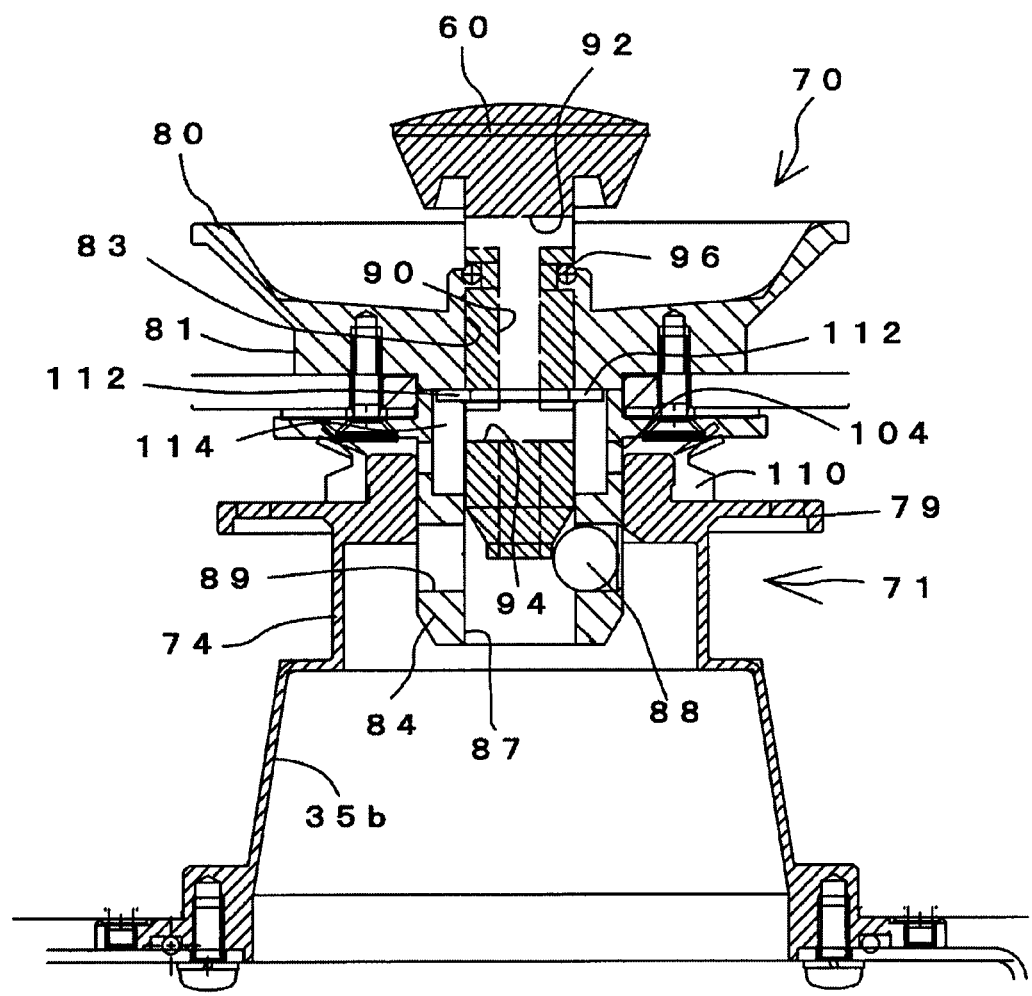
FIG. 11 is an enlarged view of the knob portion of the lid and a mounting portion of the main body

Further, FIG. 11 illustrates an enlarged mounting portion of the main body and knob portion. In a center of the lid 42, a metal knob portion 70 is provided. The knob portion 70 has two functions of a function for being gripped when an operator operates the lid 42, and a function for connecting with the main body 40.

The knob portion 70 includes a main body 81 formed with a round outer extending portion 80 in a planar view, and an axis portion 82 that is vertically movable. In a center of the main body, an insertion hole 83 is formed through which the axis portion 82 is inserted in such a manner to move vertically. Downward from the main body 81, a fixing hub 84 projecting downward is provided. The fixing hub 84 has a cylindrical shape and formed with a center hole 87 communicating with the insertion hole 83 of the main body 81.

An upper end portion of the axis portion 82 is provided with a knob large-diameter portion 60 having a diameter that becomes gradually larger upward.

A lower end portion of the axis portion 82 is formed in a tapered shape in which a diameter of the axis portion 82 becomes gradually smaller toward the leading end, and inserted into the center hole 87 of the fixing hub 84.

A side face of the fixing hub 84 is formed with a communication hole 89 for communicating the center hole 87 with an outside. In the communication hole 89, a metal ball 88 is movably provided in the hole. When the metal ball 88 is moved outward in the communication hole 89, it can project to the outside of the fixing hub 84. The communication hole 89 has a diameter that gradually becomes smaller outward. A part of the metal ball 88 projects outside the fixing hub 84, but a whole portion of the metal ball does not project outside the fixing hub 84.

According to the present embodiment, the communication holes 89 are formed at three points with equal intervals provided from one another, and the metal ball 88 is provided for each of the communication holes 89, and thus weight balance can be maintained even during being rotated.

With the metal ball 88, the lid 42 and the main body 40 are fixed with each other. In other words, when the lid 42 is fixed to the main body 40, the operator inserts the axis portion 82 into the insertion portion 78 of the mounting portion 71 of the main body 40.

Then, the side face of the leading end portion of the axis portion 82 in a tapered shape comes into contact with the metal ball 88 arranged in the communication hole 89. When the operator presses down the axis portion 82, the metal ball 88 moves outward along with lowering of the axis portion 82, and a part of the metal ball 88 projects outward from the communication hole 89.

The metal ball 88 projecting outward from the fixing hub 84 as described above comes into contact with a lower end face of the insertion portion 78 of the mounting portion 71 of the main body 40. As described above, the metal ball 88 of the fixing hub 84 comes into contact with the insertion portion 78 to fix the lid 42 to the main body 40.

An area where the axis portion 82 moves vertically is restricted by a flange portion 112 formed on a middle portion of the axis portion 82.

In other words, a predetermined point of the center hole 87 of the fixing hub 84 is formed with a large diameter portion 114 in which the flange portion 112 can be moved. When the axis portion 82 is lowered, the flange portion 112 comes into contact with a lower face of the large diameter portion 114 so that a position of the axis portion 82 becomes a lowest position. When the axis portion 82 is raised, the flange portion 112 comes into contact with an upper face of the large diameter portion 114 and the position thereof becomes a highest position.

Subsequently, a constitution in which a knob portion of the lid is formed with an air hole will be described.

There may be a case where, after the smearing processing is finished, when the lid 42 is tried to be removed from the main body 40, it cannot be removed. This occurs, because, after the sealed rotating container 34 is used, sterilization is performed with hot water or steam sterilization process is performed, and subsequently, the lid 42 is fixed to the main body 40 in a state where a temperature is still high. Thus, an inside of the sealed rotating container 34 has a negative pressure.

As described above, when the inside of the sealed rotating container 34 has the negative pressure, in order to easily remove the lid 42 from the main body 40, the present embodiment adopts a constitution described below.

Figure 12:
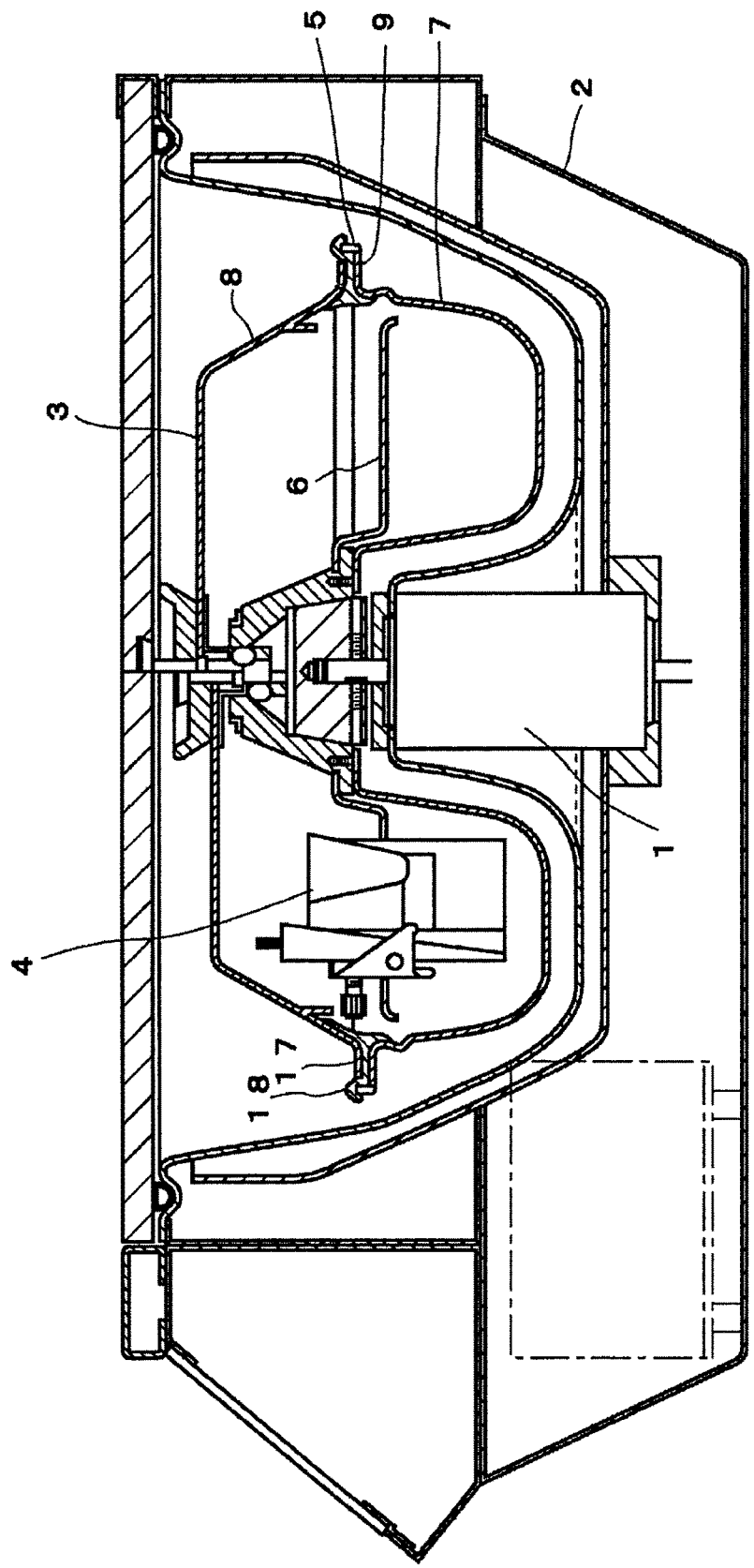
FIG. 12 is a cross-sectional view illustrating a constitution of a conventional centrifugal smearing device.

In other words, when the axis portion 82 of the knob portion 70 is lifted (moved upward), an inside and an outside of the sealed rotating container 34 are communicated with each other. More specifically, as illustrated in FIG. 12, an air hole 90 is formed in the axis portion 82 through which, when the axis portion 82 of the knob portion 70 is lifted to remove the lid 42, the inside and the outside of the sealed rotating container 34 are communicated with each other.

The air hole 90 of the axis portion 82 is formed by communicating an outer opening portion 92 formed at an upper position than an upper face of the main body 81 of the knob portion 70 when the axis portion 82 is lifted with an inner opening portion 94 positioned downward from the main body 81 of the knob portion 70 (inside of the sealed rotating container 34) when the axis portion 82 is lifted.

The outer opening portion 92 is formed at a plurality of positions on a side face of the axis portion 82, and the inner opening portion 94 is formed on a side face of a lower side thereof. The air hole 90 is formed along a center axis of the axis portion 82 to communicate the outer opening portion 92 with the inner opening portion 94.

When the axis portion 82 is raised, the communication hole 104 communicating with the inner opening portion 94 of the axis portion 82 is formed in the large diameter portion 114 of the fixing hub 84. The communication hole 104 opens to an inner wall side of a center opening portion of the "V" ring 110.

An operation of forming such an air hole 90 is described as follows.

Before the smearing process is started, when the lid 42 is mounted to the main body 40, if the operator presses the knob large-diameter portion 80 to lower the axis portion 82, the outer opening portion 92 goes into the insertion hole 83 of the main body 81 of the knob portion 70 to be hidden from the outside. Therefore, the air hole 90 is closed to seal the inside of the sealed rotating container 34.

After the smearing process is finished, when the operator pulls (raise) the knob large-diameter portion 80, the outer opening portion 92 formed in the axis portion 82 is exposed outside from the insertion hole 83. With this arrangement, the air is fed from the outside of the sealed rotating container 34 to the inside thereof via the outer opening portion 92, the air hole 90, the inner opening portion 94, and the communication hole 104.

Therefore, even if the inside of the sealed rotating container 34 has the negative pressure, when the lid 42 is removed, the air can be fed from the outside, thereby solving the problem of the negative pressure of the inside and easily removing the lid 42.

Further, an "O" ring 96 may be mounted on an outer circumference of the axis portion 82.

A mounting position of the "O" ring 96 is always located where the "O" ring 96 is arranged in the insertion hole 83 of the main body 81 of the knob portion 70. In other words, a resistance force generated between the "O" ring 96 and the insertion hole 83 is applied to the axis portion 82 when the axis portion 82 is lifted and when the axis portion 82 is pressed down.

Further, with a sliding resistance force of the axis portion 82 by the "O" ring 96, even if the operator does not hold the axis portion 82, the axis portion 82 can be held at the position by the gravity without lowering by itself.

As described above, the "O" ring 96 is provided to the axis portion 82 of the knob portion 70 so that the lid 42 and the main body 40 are fixed with one push (pressing the axis portion 82 only once). In other words, if no resistance force is applied to the axis portion 82, and when the operator does not hold the axis portion 82, the axis portion 82 is lowered due to the gravity. Thus, the axis portion 82 cannot be pushed to fix to the main body 40 without raising the axis portion 82 again.

However, as in the present embodiment, the "O" ring 96 is provided to the axis portion 82 so that, even after the lid 42 is removed, the axis portion 82 can be easily fixed to the main body 40.

As a constitution in which the axis portion 82 can be pressed down with one push to fix the lid 42 to the main body 40, in addition to mounting the "O" ring 96 on the outer circumference of the axis portion 82, for example, it can be considered to provide a spring to apply an urging force between the axis portion 82 and an inner wall face of the insertion hole 83.

However, if the sliding resistance force is applied to the axis portion 82 by the spring, when the sealed rotating container 34 vibrates, the axis portion 82 may be flown up by a slight reaction force of the spring to release the fixation between the lid 42 and the main body 40. Therefore, the "O" ring is preferable to the spring to apply the sliding resistance to the axis portion 82 in the insertion hole 83.

What is claimed is:

1. A centrifugal smearing device comprising:
    a sealed rotating container that houses a chamber with a slide glass removably attached for holding a liquid sample and smearing cells in the liquid sample onto the slide glass with a centrifugal force; and
    a base housing the sealed rotating container and having a motor for rotating the sealed rotating container,
    wherein said sealed rotating container includes a main body being capable of housing said chamber and a lid configured to close an upper face opening portion of the main body,
    wherein a packing has a section formed into a U-like shape to sandwich an end of an outer edge portion of the lid that projects in a horizontal plane, the packing mounted on a horizontal portion formed in the end face of the upper face opening portion of the main body so as to see a space between the main body and an end face of the upper face opening portion of the main body,
    wherein the lid comprises a scattering protection wall formed at an inside of a seal portion so as to protrude downward to hide the packing from inside so that a liquid does not scatter onto the packing,
    wherein the scattering protection wall projects downward from the outer edge portion, in which the packing is provided, and is formed in a ring-like space making a circle at a lower portion of the lid, and the scattering protection wall slopes toward an outside to flow a received liquid, which has been scattered onto the scattering protection wall and moved outward by a centrifugal force while performing a centrifugal-smearing, downward and toward the outside,
    wherein a storing section is provided below at an obliquely outer side of the scattering protection wall, the storing section operable to store a liquid dropping obliquely downward outside along the scattering protection wall,
    wherein a protruding portion is formed above the storing section so as to prevent a liquid stored in the storing section from moving upward, and the horizontal portion, to which the seal portion of the lid is provided, is formed above the protruding portion, and
    wherein a lower end of the scattering protection wall is extended to a lower end of the protruding portion.

2. A sealed rotating container that is used for a centrifugal smearing device and houses a chamber with a slide glass removably attached for holding a liquid sample and smearing cells in the liquid sample onto the slide glass with a centrifugal force, said sealed rotating container comprising:
    a main body being capable of housing said chamber and a lid configured to close an upper face opening portion of the main body,
    wherein a packing is formed into a U-like shape to sandwich an end of an outer edge portion of the lid that projects in a horizontal plane, the packing mounted on a horizontal portion formed in the end face of the upper face opening portion of the main body so as to seal a space between the main body and an end face of the upper face opening portion of the main body,
    wherein the lid comprises a scattering protection wall formed at an inside of the seal portion so as to protrude downward to hide the packing from inside so that a liquid does not scatter onto the packing,
    wherein the scattering protection wall projects downward from the outer edge portion, in which the packing is provided, and is formed in a ring-like shape making a circle at a lower portion of the lid, and the scattering protection wall slopes toward an outside to flow a received liquid, which has been scattered onto the scattering protection wall and moved outward by a centrifugal force while performing a centrifugal-smearing, downward and toward the outside,
    wherein a storing section is provided below at an obliquely outer side of the scattering protection wall, the storing section operable to store a liquid dropping obliquely downward outside along the scattering protection wall,
    wherein a protruding portion is formed above the storing section so as to prevent a liquid stored in the storing section from moving upward, and the horizontal portion, to which the seal portion of the lid is provided, is formed above the protruding portion, and
    wherein a lower end of the scattering protection wall is extended to a lower end of the protruding portion.

* * * * *